(12) United States Patent
Amano et al.

(10) Patent No.: US 7,294,601 B2
(45) Date of Patent: Nov. 13, 2007

(54) PHOSPHINES, TRANSITION METAL COMPLEXES CONTAINING THE SAME AS THE LIGAND, AND PROCESS FOR PRODUCTION OF OPTICALLY ACTIVE CARBOXYLIC ACIDS

(75) Inventors: Akira Amano, Kanagawa (JP); Daisuke Igarashi, Kanagawa (JP); Noboru Sayo, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 11/540,166

(22) Filed: Sep. 29, 2006

(65) Prior Publication Data

US 2007/0060772 A1    Mar. 15, 2007

Related U.S. Application Data

(63) Continuation of application No. PCT/JP2005/003117, filed on Feb. 25, 2005.

(30) Foreign Application Priority Data

Mar. 30, 2004    (JP) ............................. 2004-097508

(51) Int. Cl.
*B01J 31/00*    (2006.01)
(52) U.S. Cl. .................. 502/162; 502/116; 556/21; 562/490; 562/504; 560/179; 560/112
(58) Field of Classification Search ............... 502/162, 502/166; 556/21; 562/35, 490, 504; 560/179, 560/112; 568/15, 17, 881
See application file for complete search history.

(56) References Cited

U.S. PATENT DOCUMENTS

| 4,962,230 | A |   | 10/1990 | Takaya et al. |
|-----------|---|---|---------|---------------|
| 5,274,146 | A |   | 12/1993 | Ishizaki et al. |
| 5,536,858 | A | * | 7/1996  | Lalonde et al. ............... 556/21 |
| 5,728,866 | A | * | 3/1998  | Rautenstrauch et al. .... 560/122 |
| 5,827,794 | A | * | 10/1998 | Davis et al. ................. 502/162 |
| 6,184,413 | B1| * | 2/2001  | Davis et al. ................. 560/179 |
| 6,878,665 | B2| * | 4/2005  | Duprat de Paule et al. . 502/165 |

FOREIGN PATENT DOCUMENTS

| JP | 63-239245   |   | 5/1988  |
|----|-------------|---|---------|
| JP | 5-170780    |   | 9/1993  |
| JP | 7-252281    |   | 3/1995  |
| WO | WO 03/029259| * | 4/2003  |

OTHER PUBLICATIONS

Duprat de Paule et al., {SYNPHOS, A new chiral diphosphine ligand: synthesis, molecular modeling and application in asymmetric hydrogenation, Tetrahedron Letters (2003), 44(4), 823-826}.*

Qiu et al., {Synthesis of Novel Diastereomeric Diphosphine Ligands and Their Applications in Asymmetric Hydrogenation Reactions, Organic Letters (2002), 4(26), 4599-4602}.*
Hatano et al., {Highly enantioselective palladium-catalyzed ene-type cyclization of a 1,6-enyne, Angewandte Chemie, International Edition (2001), 40(1), 249-253}.*
Zhang et al., {Synthesis of partially hydrogenated BINAP variants, Tetrahedron Letters (1991), 32(49), 7283-6}.*
Herrmann et al., Angew. Chem. Int. Ed. Engl., 34(7):811-813 (1995).
Wan et al., Tetrahedron: Asymmetry, 4(12):2461-2468 (1993).
Amrani et al., Oranometallics, 8:542-547 (1989).
Eckl et al., Journal of Organometallic Chemistry, 532:243-249 (1997).

* cited by examiner

*Primary Examiner*—Yvonne (Bonnie) Eyler
*Assistant Examiner*—Chukwuma Nwaonicha
(74) *Attorney, Agent, or Firm*—Peter F. Corless; Christine C. O'Day; Edwards Angell Palmer & Dodge LLP

(57) ABSTRACT

[PROBLEMS] To provide a method by which desired optically active carboxylic acids may be prepared from a carboxylic acid having a carbon-carbon double bond through asymmetric hydrogenation with a catalyst consisting of a transition metal complex containing a water-soluble ligand and which permits easy separation of the used catalyst from the product by liquid-liquid separation alone and enables the recovery of an expensive transition metal and the reuse of the catalyst.

[MEANS FOR SOLVING PROBLEMS] Phosphines represented by the general formula (1):

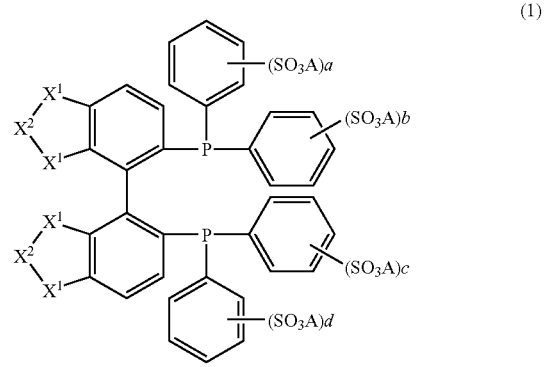

wherein $X^1$ is oxygen or methylene; $X^2$ is methylene, ethylene, trimethylene, 1,2-dimethylethylene, isopropylidene, or difluoromethylene; A is a Group IA alkali metal of the periodic table, hydrogen, or an ammonium ion; and a, b, c and d are each an integer of 0 or 1, with the proviso that the cases wherein the sum of a, b, c, and d is 0 are excepted.

8 Claims, No Drawings

PHOSPHINES, TRANSITION METAL COMPLEXES CONTAINING THE SAME AS THE LIGAND, AND PROCESS FOR PRODUCTION OF OPTICALLY ACTIVE CARBOXYLIC ACIDS

CROSS-REFERENCE TO RELATED APPLICATION(S)

This application is a continuation application of PCT/JP2005/003117 filed Feb. 25, 2005, which PCT application claims priority from Japanese Application number 2004-097508 filed Mar. 30, 2004, each of which applications are incorporated herein by reference in their entirety.

TECHNICAL FIELD

The present invention relates to a phosphine compound, which is useful as a catalyst in various kinds of organic synthetic reactions, especially in asymmetric hydrogenation reaction, to a transition metal complex containing it as a ligand, and to a method for producing an optically active carboxylic acid.

BACKGROUND ART

A transition metal complex containing a phosphine compound as a ligand, especially a chiral phosphine compound, plays an extremely important role supporting stereo-selective production of organic compounds in various fields such as such as perfumes, pharmaceuticals, agricultural chemicals, and liquid crystals.

On the other hand, as to these catalysts, since transition metals to be used are expensive, reduction of used amount, or development of methods for recovering thereof had been demanded, and many methods already have been reported.

A method wherein a phosphine ligand is converted to a water-soluble derivative, a reaction is carried out in an aqueous solution using a transition metal complex thereof, a product is taken out by separation, and thereafter, the residual aqueous phase is reused for a next reaction, is one of means solving for this problem. As a method for making a water-soluble phosphine ligand, various methods are attempted, and when aryl phosphines are taken as an example, sulfonation of an aromatic ring such as a phenyl group and a naphthalene ring in a molecule, is most often used.

For example, in Non-Patent Document 1, three phenyl groups of triphenylphosphine are substituted with two or three sulfonic acid groups and substituted with eight sulfonic acid groups, are reported.

Further, in Patent Document 1, BINAP wherein 5 and 5' positions of a bi-naphthyl group are sulfonated, and in Non-Patent Document 2, BINAP wherein all of four phenyl groups are sulfonated, are respectively described.

In Non-Patent Document 3, four ligands of (S, S)-cyclobutanediop, (S, S)-Chiraphos, (S, S)—BDPP, and (R)-Prophos which are tetra-sulfonated, are reported. In Non-Patent Document 4, a sulfonated diphosphine ligand NAPHOS are reported.

Non-Patent Document 1: Angew. Chem. Int. Ed. Engl., 1995, 34, No. 7, pp. 811-3,

Non-Patent Document 2: Tetrahedron Asymmetry, Vol. 4, No. 12, pp. 2461-8(1993),

Non-Patent Document 3: Organometallics, 1989, No. 8, pp. 542-7,

Non-Patent Document 4: Journal of Organometallic Chem. 532 (1997) pp. 243-9, and Patent Document 1: JP-A-5-170-780.

DISCLOSURE OF THE INVENTION

Problems to be Solved by the Invention

However, some water-soluble phosphine compounds known in the prior art do not bring satisfactory results depending on kinds of reaction substrates applied thereto, and further various kinds of phosphine compounds are desired.

The present invention was made by considering the above-described problems, and it is an object to provide a method for producing desired optically active carboxylic acids which may be obtained by an asymmetric hydrogenation reaction using a water-soluble catalyst, the method that the used catalyst may be easily separated by liquid-liquid separation alone.

Means for Solving the Problems

Namely, the present invention includes each of the inventions [1] to [6] as follows.

[1] A phosphine compound represented by the general formula (1),

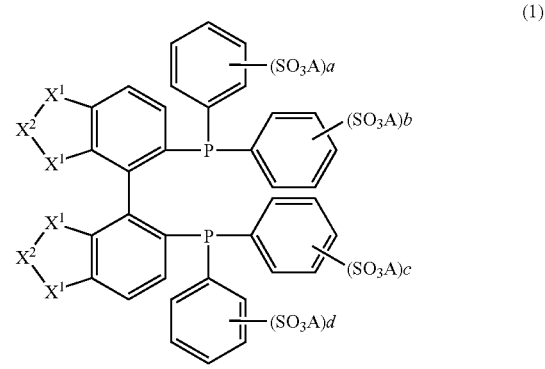

(1)

(wherein $X^1$ represents oxygen atom or methylene group; $X^2$ represents methylene group, ethylene group, trimethylene group, 1,2-dimethylethylene group, isopropylidene group or difluoromethylene group; A is Group IA alkali metal of the periodic table, hydrogen atom, or an ammonium ion; and a, b, c and d are each an integer of 0 or 1, with the proviso that the cases wherein the sum of a, b, c, and d is 0 are excluded).

[2] The phosphine compound according to [1], which is an optically active substance.

[3] A transition metal complex which has a phosphine compound according to [2] as a ligand.

[4] A method for production of an optically active carboxylic acid wherein asymmetric hydrogenation of a carboxylic acid compound having a carbon-carbon double bond is carried out in the presence of the transition metal complex according to [3].

[5] The method for production according to [4], wherein the transition metal complex is prepared in a reaction system of asymmetric hydrogenation reaction.

[6] The method for production according to [4] or [5], wherein the transition metal complex as an aqueous solution is recovered from a reaction solution obtained after completion of a reaction, and the aqueous solution is recycled to the reaction system.

[7] The method for production according to any one of [4] to [6], wherein the carboxylic acid compound having a carbon-carbon double bond, is a compound represented by the general formula (2),

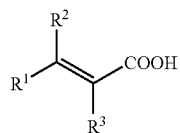

(2)

(wherein $R^1$, $R^2$ and $R^3$ represent hydrogen atom, linear or branched or cyclic alkyl group, aromatic hydrocarbon group which may have substituent (s), heterocyclic group which may have substituent (s), acyloxy group, acylamino group, alkoxy group, aryloxy group, alkoxycarbonyl group, carboxyl group, furyloxy group, thienyloxy group, or $R^1$ and $R^2$, or $R^1$ and $R^3$ may form a divalent group —$(CH_2)_m$—$X^3$—$(CH_2)_n$— (where $X^3$ represents methylene group, nitrogen atom, oxygen atom or sulfur atom; and m represents 1 or 2, and n is an integer of 0 to 3); with a proviso that $R^1$ and $R^2$ are not the same group, and $R^1$ and $R^3$ are not a hydrogen atom at the same time), and the optically active carboxylic acid is represented by the general formula (3),

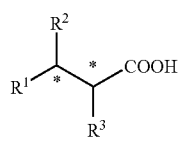

(3)

(wherein $R^1$, $R^2$ and $R^3$ represent the same meanings as described above, and * represents one or the both of them being an asymmetric carbon).

EFFECT OF THE INVENTION

An asymmetric hydrogenation reaction using a water-soluble complex as a catalyst, which has an optically active phosphine compound according to the present invention as a ligand, enables recycling of a catalyst, and it leads to decrease of wastes and reductions in cost. Further, the asymmetric hydrogenation reaction using an optically active water-soluble complex according to the present invention as a catalyst, can be carried out in a water-based solvent. Therefore, it is also possible to reduce used and waste amount of a solvent which damages the environment.

BEST MODE FOR CARRYING OUT THE INVENTION

In a phosphine compound represented by the above-described general formula (1), a Group IA alkali metal of the periodic table represented by A includes lithium, sodium, potassium, rubidium, cesium, and the like. An ammonium ion represented by A includes those represented by the general formula (4) or (5) described below,

 (4)

 (5)

(In the formulae (4) and (5) wherein $R^4$, $R^5$ and $R^6$ each represent independently hydrogen atom, alkyl group or aralkyl group and Ht represents a nitrogen-containing heterocyclic ring).

Here, an alkyl group includes a linear, branched, or cyclic alkyl group, and specifically includes methyl, ethyl, n-propyl, isopropyl, n-butyl, n-hexyl, n-octyl, n-decyl, n-hexadecyl, cyclohexyl, and the like. An aralkyl group includes benzyl, 1-phenylethyl, and the like.

A nitrogen-containing heterocyclic ring represented by Ht includes nitrogen-containing heterocyclic rings of a saturated or unsaturated 5-membered ring or 6-membered ring, and specifically includes pyridine ring, pyrrolidine ring, piperidine ring, morpholine ring, imidazole ring, and the like.

The phosphine compound according to the present invention, represented by the general formula (1), can be synthesized, for instance, in a method described below:

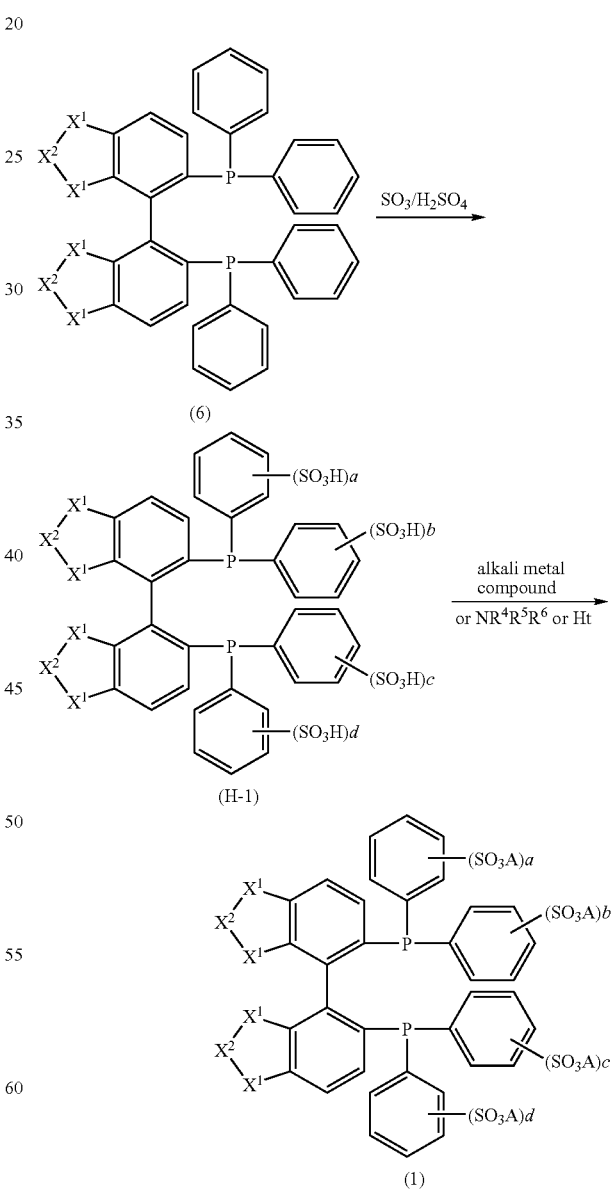

(In the scheme, $X^1$, $X^2$, A, a, b, c, d, $R^4$, $R^5$, $R^6$ and Ht represent the same meanings as described above.)

That is, a sulfuric acid solution of a fuming sulfuric acid is added to the phosphine compound (6), and then a phenyl group on phosphine atom is sulfonated to synthesize a sulfonic acid compound (H-1), followed by adding an alkali metal compound or ammonia or amines to obtain the compound (1) of the present invention as an alkali metal salt or an ammonium salt.

Here, when $X^1$ is an oxygen atom, the phosphine compound (6) which is a raw material compound, for instance as described in Patent Document 2, is synthesized by using 3,4-methylenedioxy-bromobenzene as a starting material, through introducing a phosphine atom, a coupling reaction and optical resolution, and the like. Further, when $X^1$ is methylene, for instance as described in Patent Document 3, the phosphine compound is synthesized from 2,2'-dihalogeno-1,1'-binaphthyl, by partially hydrogenating a binaphthyl ring in the presence of a transition metal catalyst, through introduction of a phosphine atom, optical resolution, and the like.

Patent Document 2: JP-A-10-182678, and

Patent Document 3: JP-A-4-139140.

All of reaction operations are preferred to be carried out in an inert gas atmosphere such as nitrogen, argon, or the like to prevent oxidation of a phosphine compound.

In sulfonation of the first step, a molar ratio of a concentrated sulfuric acid and 30% of a fuming sulfuric acid (30% $SO_3$—$H_2SO_4$) is selected from the range of 1:0.8 to 1:1.2, preferably from the range of 1:1 to 1:1.1.

A molar ratio of $SO_3$ in 30% of a fuming sulfuric acid and the phosphine compound (6) is selected from the range of 60:1 to 30:1, more preferably from the range of 40:1 to 50:1.

A reaction temperature is preferred to be not higher than room temperature, and preferably is in the range of 0° C. to 25° C., more preferably in the range of 0° C. to 10° C., to keep to a minimum oxidation of the phosphine compound (6) with $SO_3$ in a fuming sulfuric acid to the minimum.

A reaction time is preferably not longer than one week when a reaction temperature is about 20° C., and when the reaction time becomes longer, the amount of phosphine oxides which are obtained by oxidizing a phosphine atom is increased. It is preferred to be in the range of one week to three weeks when the temperature is not higher than 10° C., and is more preferred to be in the range of 10 days to two weeks when the temperature is about 5° C.

After a sulfonation reaction, the phosphine compound (1) of the present invention may be derived by neutralizing an excess of sulfuric acid with an alkali metal compound or ammonia or amines, as well as by substituting a hydrogen atom of a sulfonic acid group with an alkali metal or an ammonium ion.

Here, an alkali metal compound to be used includes hydroxides, carbonates, alkoxides, phosphates, and the like. These alkali metal compounds may be used in a solution such as an aqueous solution. Specific compounds, though not limited to these, include sodium hydroxide, potassium hydroxide, lithium hydroxide, cesium hydroxide, rubidium hydroxide, lithium carbonate, sodium carbonate, potassium carbonate, rubidium carbonate, cesium carbonate, sodium bicarbonate, potassium bicarbonate, sodium methoxide, sodium ethoxide, sodium phenoxide, sodium tert-butoxide, potassium tert-butoxide, lithium methoxide, lithium phosphate, potassium phosphate, sodium phosphate, potassium hydrogen phosphate and sodium hydrogen phosphate, and the like.

As amines used herein, aliphatic and aromatic, cyclic or linear, primary, secondary and tertiary amines are used. Specific compounds include ammonia, methylamine, dimethylamine, trimethylamine, ethylamine, diethylamine, triethylamine, propylamine, diisopropylamine, ethyldiisopropylamine, tributylamine, trioctylamine, cyclohexylamine, benzylamine, pyridine, picoline, pyrrolidine, N-methylpyrrolidine, piperidine, N-methylpiperidine, morpholine, N-methylmorpholine, imidazole and N-methylimidazole, and the like.

After neutralizing an excess amount of sulfuric acid, operation for removing water by distillation from a reaction mixture is necessary to efficiently separate the water-soluble sulfonated phosphine compound (1) of the present invention and sulfates by an organic solvent.

Extraction of the sulfonatedphosphine compound (1) by an organic solvent may be carried out with methanol, ethanol, n-propanol, isopropanol, n-butanol, aqueous methanol, aqueous ethanol, or the like. Among these, more preferably, aqueous methanol and n-butanol are exemplified.

The sulfonated phosphine compound (1) synthesized as above may be prepared to a transition metal complex compound without further purification.

A transition metal forming a complex includes rhodium (Rh), ruthenium (Ru), iridium (Ir), palladium (Pd), nickel (Ni), copper (Cu), and the like.

These transition metal complexes are represented by the general formula (7) described below:

$$M_mL_nW_pU_q \qquad (7)$$

(wherein M represents a transition metal selected from the group consisting of Ir, Rh, Ru, Pd and Ni; L represents an optically active phosphine compound (1) of the present invention; and m, n, p and q represents an integer as follows)

In case where M represents Ir or Rh, as to W, U, m, n, p and q, W represents a chlorine atom (Cl), a bromine atom (Br) or an iodine atom (I), and m=n=p=2, and q=0;

In case where M is Ru, (i) W represents Cl, Br or I, and U represents a trialkylamino group, and m=n=2, p=4 and q=1; (ii) W represents Cl, Br or I, and U represents pyridine, picoline or quinoline, and m=n=1, p=q=2; (iii) W is a carboxylate group, and m=n=1, p=2 and q=0; (iv) W is Cl, Br or I, and m=n=1, p=2 and q=0; and (v) Wi s Cl, Br or I, and U represents dialkylammonium, and m=n=2, p=5, and q=1;

In case where M is Pd, (i) W is Cl, Br or I, and m=n=1, p=2, and q=0; and (ii) W is an allyl group, and m=n=p=2, and q=0;

In case where M is Ni, W is Cl, Br or I, and m=n=1, p=2, and q=0).

Further, the transition metal complexes according to the present invention are also represented by the general formula (8) described below:

$$[M_mL_nW_pU_q]Z_s \qquad (8)$$

(wherein M represents a transition metal selected from the group consisting of Ir, Rh, Ru, Pd and Ni; L represents an optically active phosphine compound (1) according to the present invention; and m, n, p, q and s represent an integer as follows;

In case where M is Ir or Rh, W is 1, 5-cyclooctadiene (hereinafter called as "cod"), or norbornadiene (hereinafter called as "nbd"), Z represents $BF_4$, $ClO_4$, $CF_3SO_3$ (hereinafter called as "OTf"), $PF_6$, $SbF_6$ or $BPh_4$ (Ph represents a phenyl group, and hereinafter the same.), and m=n=p=s=1, and q=0;

In case where M is Ru, (i) W is Cl, Br or I, and U represents an aromatic compound or an olefinic compound which is a neutral ligand, Z is Cl, Br, I, I$_3$ or sulfonate, and m=n=p=q=s=1; (ii) Z is BF$_4$, ClO$_4$, OTf, PF$_6$, SbF$_6$ or BPh$_4$, and m=n=1, p=q=0, and s=2;

In case where M is Pd or Ni, Z is BF$_4$, ClO$_4$, OTf, PF$_6$, SbF$_6$ or BPh$_4$, and m=n=1, p=q=0, and s=2).

These transition metal complexes according to the present invention may be parepared by using a known method.

Rhodium Complex:

A rhodium complex may be obtained, for example, by reacting [Rh(cod)$_2$]BF$_4$ and an optically active sulfonated phosphine compound (1) of the present invention in accordance with the method as described in Non Patent Document 5.

Non Patent Document 5: "Fourth Edition: Jikken Kagaku Kouza" edited by Japan Chemical Society, Vol. 18, Organic metal complex, 1991, published by Maruzen, pp.339-344

Specific examples of the rhodium complex include, for example, the following:

[Rh(L)Cl]$_2$, [Rh(L)Br]$_2$, [Rh(L)I]$_2$, [Rh(cod)(L)]OTf, [Rh(cod)(L)]BF$_4$, [Rh(cod)(L)]ClO$_4$, [Rh(cod)(L)]SbF$_6$, [Rh(cod)(L)]PF$_6$, [Rh(cod)(L)]BPh$_4$, [Rh(nbd)(L)]OTf, [Rh(nbd)(L)]BF$_4$, [Rh(nbd)(L)]ClO$_4$, [Rh(nbd)(L)]SbF$_6$, [Rh(nbd)(L)]PF$_6$, and [Rh(nbd)(L)]BPh$_4$.

Ruthenium Complex:

A ruthenium complex may be prepared, for example, by stirring [Ru(cod)Cl$_2$]$_n$ and an optically active sulfonated phosphine compound (1) of the present invention in the presence of a trialkylamine in a solvent in accordance with the method as described in Non Patent Document 6. Alternatively, the ruthenium complex may be prepared by stirring [Ru(benzene)Cl$_2$]$_2$ and an optically active phosphine compound (1) of the present invention in the presence of a dialkylamine in a solvent in accordance with the method as described in Patent Document 4. Further, the ruthenium complex may be prepared by stirring [Ru(p-cymene)I$_2$]$_2$ and an optically active phosphine compound (1) of the present invention in a solvent in accordance with the method as described in Non-Patent Document 7.

Non Patent Document 6: J. Chem. Soc., Chem. Commun., 922 (1985),

Patent Document 4: JP-A-11-269285, and

Non Patent Document 7: J. Chem. Soc., Chem. Commun., 1208 (1989).

Specific examples of the ruthenium complex include, for example, the following (Ac represents an acetyl group, and Ph represents a phenyl group. Hereinafter the same): Ru(OAc)$_2$(L), Ru(OCOCF$_3$)$_2$(L), Ru$_2$Cl$_4$(L)$_2$NEt$_3$, [{RuCl(L)}$_2$(μ-Cl$_3$)[Me$_2$NH$_2$], [{RuBr(L)}$_2$(μ-Br$_3$)[Me$_2$NH$_2$], [{RuI(L)}$_2$(μ-I$_3$)[Me$_2$NH$_2$], [{RuCl(L)}$_2$(μ-Cl$_3$)[Et$_2$NH$_2$], [{RuBr(L)}$_2$(μ-Br$_3$)[Et$_2$NH$_2$], [{RuI(L)}$_2$(μ-I$_3$)[Et$_2$NH$_2$], RuCl$_2$(L), RuBr$_2$(L), RuI$_2$(L), RuCl$_2$(pyridine), RuBr$_2$(pyridine), RuI$_2$(pyridine), [RuCl(benzene)(L)]Cl, [RuBr(benzene)(L)]Br, [RuI(benzene)(L)]I, [RuCl(p-cymene)(L)]Cl, [RuBr(p-cymene)(L)]Br, [RuI(p-cymene)(L)]I, [Ru(L)](OTf)$_2$, [Ru(L)](BF$_4$)$_2$, [Ru(L)](ClO$_4$)$_2$, [Ru(L)](SbF$_6$)$_2$, [Ru(L)](PF$_6$)$_2$, and [Ru(L)](BPh$_4$)$_2$.

Iridium Complex:

An iridium complex may be prepared, for example, by stirring an optically active sulfonated phosphine compound (1) of the present invention and [Ir(cod)(CH$_3$CN)$_2$]BF$_4$ in a solvent in accordance with the method as described in Non Patent Document 8.

Non Patent Document 8: J. Organomet. Chem., 1992, 428, 213

Specific examples of the iridium complex include, for example, the following:

[Ir(L)Cl]$_2$, [Ir(L)Br]$_2$, [Ir(L)I]$_2$, [Ir(cod)(L)]OTf, [Ir(cod)(L)]BF$_4$, [Ir(cod)(L)]ClO$_4$, [Ir(cod)(L)]SbF$_6$, [Ir(cod)(L)]PF$_6$, [Ir(cod)(L)]BPh$_4$, [Ir(nbd)(L)]OTf, [Ir(nbd)(L)]BF$_4$, [Ir(nbd)(L)]ClO$_4$, [Ir(nbd)(L)]SbF$_6$, [Ir(nbd)(L)]PF$_6$, and [Ir(nbd)(L)]BPh$_4$.

Palladium Complex:

A palladium complex may be prepared by reacting an optically active sulfonated phosphine compound (1) of the present invention and n-allyl palladium chloride according to the method as described in Non Patent Document 9.

Non Patent Document 9: J. Am. Chem. Soc., 1991, 113, 988

Specific examples of the palladium complex include, for example, the following:

PdCl$_2$(L), PdBr$_2$(L), PdI$_2$(L), Pd(OAc)$_2$(L), Pd(OCOCF$_3$)$_2$(L), [(π-allyl)Pd(L)]Cl, [(π-allyl)Pd(L)]Br, [(π-allyl)Pd(L)]I, [(π-allyl)Pd(L)]OTf, [(π-allyl)Pd(L)]BF$_4$, [(π-allyl)Pd(L)]ClO$_4$, [(π-allyl)Pd(L)]SbF$_6$, [(π-allyl)Pd(L)]PF$_6$, [(π-allyl)Pd(L)]BPh$_4$, [Pd(L)](OTf)$_2$, [Pd(L)](BF$_4$)2, [Pd(L)](ClO$_4$)$_2$, [Pd(L)](SbF$_6$)$_2$, [Pd(L)](PF$_6$)$_2$, [Pd(L)](BPh$_4$)$_2$, PhCH$_2$Pd(L)Cl, PhCH$_2$Pd(L)Br, PhCH$_2$Pd(L)I, PhPd(L)Cl, PhPd(L)Cl, and PhPd(L)Cl.

Nickel Complex:

A nickel complex may be prepared, for example, by stirring an optically active sulfonated phosphine compound (1) of the present invention and nickel chloride in a solvent in accordance with the method as described in the above-described Non Patent Document 9.

Specific examples of the nickel complex include, for example, the following: NiCl$_2$(L), NiBr$_2$(L) and NiI$_2$(L).

As an organic solvent on preparing these transition metal complexes, a solvent which has high solubility of the sulfonated phosphine compound (1) of the present invention is preferable, and more preferably is a degassed lower alkanol, and methanol is more preferable.

Consecutively, a method for production of optically active carboxylic acid according to the present invention is explained.

In case where a transition metal complex having the optically active sulfonated phosphine compound (1) of the present invention as a ligand is used as a catalyst of asymmetric hydrogenation reaction, it may be used after enhancing purity of the complex by a purification method such as concentration, vacuum concentration, solvent extraction, washing, recrystallization, or the like, and it may be used without purifying the complex. Further, a reaction may be carried out after adding a transition metal compound which are precursors of the complex and the phosphine compound (1) into a hydrogenation reaction system, respectively, and in this case, catalytic activity is sometimes improved by stirring for a proper time before adding a carboxylic acid compound having a carbon-carbon double bond as a substrate.

Specific examples of the carboxylic acid compound having a carbon-carbon double bond, which is a raw material of a method for production of an optically active carboxylic acid of the present invention, include compounds represented by the general formula (2) below:

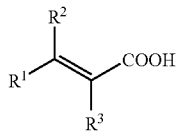

(2)

(wherein $R^1$, $R^2$ and $R^3$ represent hydrogen atom, linear, branched or cyclic alkyl, aromatic hydrocarbon which may have substituent (s), heterocyclic group which may have substituent (s), acyloxy group, acylamino group, alkoxy group, aryloxy group, alkoxycarbonyl group, carboxyl group, furyloxy, thienyloxy, or $R^1$ and $R^2$, or $R^1$ and $R^3$ may form a divalent group —$(CH_2)_m$—$X^3$—$(CH_2)_n$— (where $X^3$ represents methylene group, nitrogen atom, oxygen atom or sulfur atom; and m represents 1 or 2, and n represents an integer of 0 to 3); with a proviso that $R^1$ and $R^2$ are not the same group, and $R^1$ and $R^3$ are not a hydrogen atom at the same time)

Here, as the alkyl group, a linear, branched or cyclic alkyl group having 1 to 8 carbon atoms is preferable. Specific alkyl groups includes methyl, ethyl, n-propyl, isopropyl, n-butyl, isobutyl, 2-butyl, tert-butyl, n-pentyl, neopentyl, tert-pentyl, n-hexyl, 2-ethylhexyl, n-heptyl, n-octyl, cyclopropyl, cyclobutyl, cyclopentyl, methylcyclopentyl, cyclohexyl, methylcyclohexyl, and the like.

The aromatic hydrocarbon group of the aromatic hydrocarbon group which may have substituent (s) includes a phenyl group and a naphthyl group. The substituent substituted on these aromatic hydrocarbon groups includes alkyl, alkoxy, halogen, and the like. As the alkyl group, for example, alkyl groups as described above are exemplified.

The alkoxy group includes, for example, an alkoxy group having 1 to 8 carbon atoms, and specifically includes methoxy, ethoxy, n-propoxy, isopropoxy, n-butoxy, isobutoxy, 2-butoxy, tert-butoxy, n-pentyloxy, n-hexyloxy, and the like.

The halogen atom includes fluorine, chlorine, bromine and iodine.

The heterocyclic group of the heterocyclic group which may have substituent(s) includes furyl, thienyl, pyrrolyl, oxazolyl, thiazolyl, imidazolyl, pyridyl, pyrimidinyl, pyrazinyl, pyrrolidinyl, piperidinyl, morpholinyl, morpholino, indolyl, benzofuryl, benzothienyl, quinolyl and carbazolyl, and the like. The substituent(s) substituted on these heterocyclic groups includes alkyl, alkoxy, halogen, and the like, and specific examples thereof include those as described before.

The acyloxy group includes, for example, an acyloxyl group having 2 to 18 carbon atoms, which is derived from a carboxylic acid, and specifically includes acetoxy, propionyloxy, butyryloxy, pivaloyloxy, pentanoyloxy, hexanoyloxy, lauroyloxy, stearoyloxy, benzoyloxy, and the like.

The acylamino group includes an amino group wherein one hydrogen atom of an amino group is substituted with an acyl group as described above, and specifically includes formylamino, acetylamino, propionylamino, pivaloylamino, pentanoylamino, hexanoylamino, benzoylamino, and the like.

The aryloxy group includes a group wherein an oxygen atom has combined with an aryl group as described above, and specifically includes phenyloxy, tolyloxy, naphtyloxy, and the like. The alkoxycarbonyl group includes, for example, an alkoxycarbonyl group having 2 to 19 carbon atoms, which may be a linear, branched or cyclic one, and specifically includes methoxycarbonyl, ethoxycarbonyl, n-propoxycarbonyl, 2-propoxycarbonyl, n-butoxycarbonyl, tert-buoxycarbonyl, pentyloxycarbonyl, hexyloxycarbonyl, 2-ethylhexyloxycarbonyl, lauryloxycarbonyl, stearyloxycarbonyl, cyclohexyloxycarbonyl, and the like.

Next, the asymmetric hydrogenation method is explained. A carboxylic acid compound having a carbon-carbon double bond, which is a substrate subjected to an asymmetric hydrogenation, is hydrogenated in a solvent including water; alcohol solvent such as methanol, ethanol, or isopropanol; ether solvent such as tetrahydrofuran or diisopropyl ether; halogenated hydrocarbon such as methylene chloride; ketones such as acetone or methyl isobutyl ketone; esters such as ethyl acetate or butyl acetate; hydrocarbons such as toluene or xylene; or acetonitrile, or the like, alone or in a mixed solvent of these, after adding a $\frac{1}{1,000}$ to $\frac{1}{300,000}$ moles of catalyst, preferably $\frac{1}{10,000}$ to $\frac{1}{50,000}$ moles of catalyst based on a substrate, under a hydrogen pressure of 1 to 10 MPa, preferably of 1.5 to 5 MPa, at a temperature of 20 to 100° C., preferably 20 to 80° C., for 1 to 30 hours, preferably 2 to 20 hours, to obtain an optically active carboxylic acid.

In case where water is used as a reaction solvent, an amount of water used is appropriately selected from the range of usually 1 to 10 times, preferably 2 to 5 times, based on the amount of a carboxylic acid compound having a carbon-carbon double bond.

After completion of the reaction, in case where only water is used as a solvent on asymmetric hydrogenation reaction, a solvent which has low solubility to water but in which a product is soluble, is added into the system to separate a product and a catalyst. Alternatively, in case where only an organic solvent is used as a solvent on asymmetric hydrogenation reaction, water is added to dissolve a catalyst, and a product and a catalyst may be easily separated by separation of liquid of organic layer wherein the product is dissolved and liquid of water layer wherein the catalystis dissolved. When a reaction is carried out in a mixed system of water and an organic solvent as a solvent, a product and a catalyst may be separated by separating liquids as they are, after completion of the reaction.

Here, the separated catalyst may be recycled as an aqueous solution as it is or if necessary, after water is removed. In case that the catalyst is recycled, it is desirable that separation of a water layer wherein a catalyst is dissolved and an organic layer wherein a product is dissolved be conducted under an atmosphere of inert gas such as nitrogen or argon, to prevent decrease of catalytic activity.

Moreover, an optically active carboxylic acid represented by the general formula (3) which may be obtained by asymmetric hydrogenation according to the present invention, has one or two asymmetric points depending on structures of a substrate, and the method of present invention includes both cases of them.

EXAMPLES

Hereinafter, the present invention is more specifically explained by referring to Examples, and the present invention is not limited to these Examples.

Instruments for analysis are as follows.

1) Gas chromatography: Agilent 6890 TC-WAX, Chirasil-DEX-CB,

2) Specific optical rotation: JASCO Corporation, JASCO DIP-360 type of optical rotation meter

3) $^1H$, $^{31}P$-NMR: BURUKER DRX-500

4) HPLC:HITACHI L-7000, Cosmosil 5C8

5) LC-MS: JEOL LC mate, ZORBAX Eclipse XDB-CB C8

Example 1

Synthesis of a sodium salt of sulfonated (R)—H$_8$—BINAP ((R)—SO$_3$Na—H$_8$—BINAP):

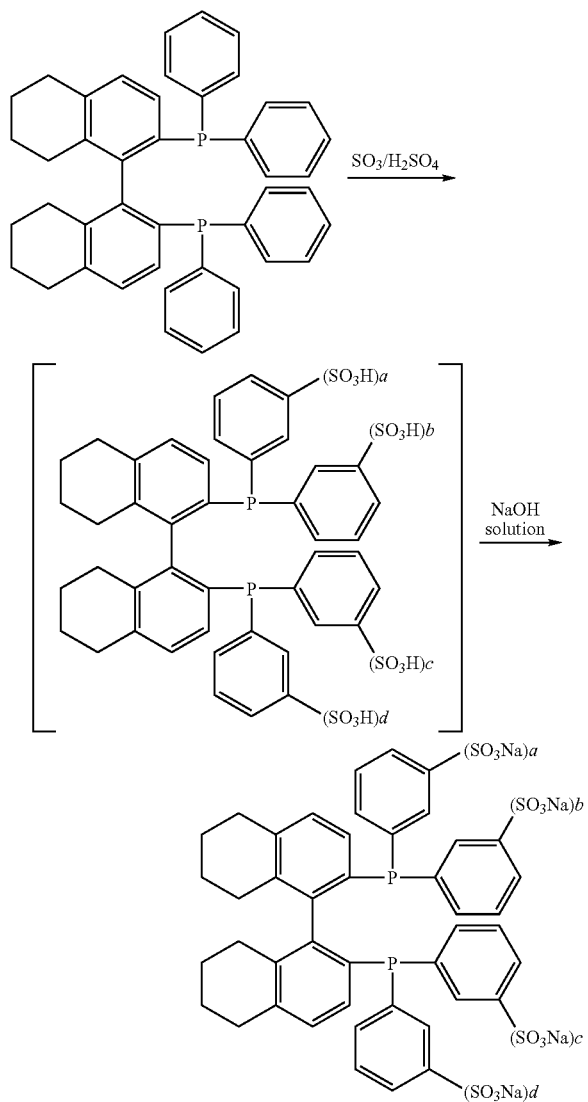

a, b, c and d represents 0 or 1, but a=b=c=d=0 is excluded.

Under a nitrogen atmosphere, 2.52 g (4 mmol) of (R)-5,6,7,8,5',6',7',8'-octahydro-2,2'-bis(diphenylphosphino)-1,1'-binaphthyl((R)—H$_8$—BINAP) was added into 3.68 g (2 mL, 37.55 mmol) of a cooled concentrated sulfuric acid at 0 to 5° C. and the mixture was stirred. 35.8 g (20 mL, 375.5 mmol) of 30% SO$_3$—H$_2$SO$_4$ was poured thereto by using a syringe. The cooling device was removed, and the temperature was raised up to room temperature while stirring. The reaction solution changed from a slurry state to a homogeneous solution in about one hour. After further stirring at room temperature for one hour, the reaction flask was sealed with filling a nitrogen, was entered into a cold room of 5° C., and was left to stand for two weeks.

Consecutively, the reaction solution was slowly added into a flask under a nitrogen atmosphere containing 200 g of crushed ice.

Hereinto, about 80 g of degassed 50% of aqueous NaOH solution was dropped with keeping at not higher than 15° C., and the reaction solution was neutralized to pH of 7.5. The neutralized aqueous solution was evaporated under a reduced pressure to remove water completely, and to obtain 62 g of ash gray aggregated solid. After the solid was collected and crushed, it was put into a reaction vessel, and filled with a nitrogen. 140 mL of degassed methanol containing 10% of water was added thereto and the mixture was stirred for one hour to extract (R)—SO$_3$Na—H$_8$—BINAP. This aqueous methanol solution was filtrated with Celite to remove sulfates, and thereafter it was concentrated by evaporation under a reduced pressure to obtain 3.2 g of (R)—SO$_3$Na—H$_8$—BINAP (pale brownish white powder). By HPLC analysis, it was proved that a ratio of those substituted with two SO$_3$Na groups was 32%, and a ratio of those substituted with three SO$_3$Na groups was 53%. A yield in case where an average molecular weight was presumed to be 900 was 88.9%. Specific optical rotation $[\alpha]_D^{20}$ was +39.8(c=1, degassed H$_2$O).

LC-MS(HPLC: ZORBAX Eclipse XDB-CB C8, an aqueous solution of methanol and dibutylamine, APCI negative mode, m/z): 788.7 (an anion formed from a divalent anion obtained by removing two Na atoms from a sodium salt of disulfonated H$_8$—BINAP and one hydrogen atom), 919 (an anion formed from a divalent anion obtained by removing two Na atoms from a sodium salt of disulfonated H$_8$—BINAP, and each one of a hydrogen atom and a dibutylamine), 868.7 (an anion formed from a trivalent anion obtained by removing three Na atoms from a sodium salt of trisulfonated H$_8$—BINAP and two hydrogen atoms), 997.8 (an anion formed from a trivalent anion obtained by removing three Na atoms from a sodium salt of trisulfonated HB$_8$—BINAP, and each one of a hydrogen atom and a dibutylamine);

$^1$H-NMR (CD$_3$OD) δ: 0.82-1.00 (2H, broads), 1.21-1.38 (2.7H, broad s), 1.68-1.38 (5.7H, broad s), 1.78-1.86 (2.5H, broad s), 2.6-2.77 (3H, broad m), 6.93-7.07 (3H, m), 7.1-7.25 (5.6H, m), 7.26-7.42 (7.1H, m), 7.63-7.74 (1.4H, m), 7.78-7.98 (4.7H, m); and $^{31}$P-NMR (CD$_3$OD) δ: −15.56, −15.86, +35.3 (P=O, <10%).

Example 2

Synthesis of a sodium salt of sulfonated (R)-segphos ((R)—SO$_3$Na-segphos):

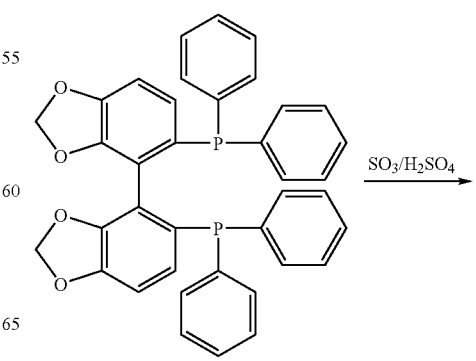

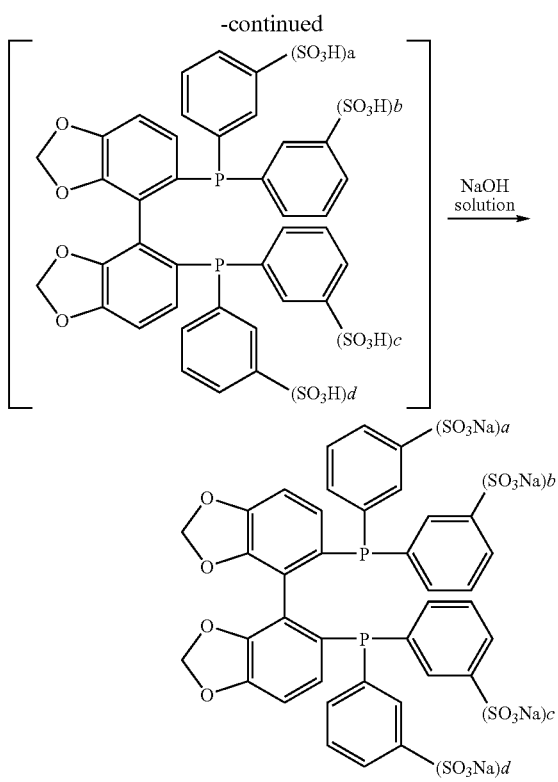

a, b, c and d represents 0 or 1, but a=b=c=d=0 is excluded.

Under a nitrogen atmosphere, 0.61 g (1 mmol) of (R)-(4, 4'-bi-1,3-benzodioxole)-5,5'-diyl-bis(dipheny lphosphine) ((R)-segphos) was added into 0.92 g (0.5 mL, 9.4 mmol) of a cooled concentrated sulfuric acid while cooling with ice, and then the mixture was stirred, next 9.2 g (5 mL, 94 mmol) of 30% $SO_3$—$H_2SO_4$ was added thereto by a syringe. After the cooling device was removed, the reaction solution was raised up to 20° C. with stirring, and changed from a slurry state to a homogeneous solution in about 1.5 hour. After the reaction flask was sealed with filling a nitrogen, it was put in a cold room of 5° C., and was left to stand for two weeks.

A flask containing 50 g of crushed ice was filled with a nitrogen and the reaction solution was slowly added thereto. Hereinto, about 20 g of degassed 50% of an aqueous NaOH solution was dropped by keeping at not higher than 15° C., and the reaction solution was brought to weak alkaline having pH of 7.5. The aqueous solution obtained was evaporated under a reduced pressure to completely remove water, and to obtain 15 g of ash gray aggregated solid. After the solid was collected and crushed, it was put into a reaction vessel and filled with a nitrogen. 30 mL of degassed methanol containing 10% of water was added thereto, and the mixture was stirred for one hour to extract (R)—$SO_3Na$—$H_8$-segphos. The aqueous methanol solution was filtrated with Celite to remove sulfates, and thereafter was concentrated by evaporation under a reduced pressure to obtain 2.2 g of (R)—$SO_3Na$—$H_8$-segphos (pale brownish white aggregated solid). Next, the aggregated solid was powdered, and then mixed with 22 mL of degassed methanol containing 10% of water, followed by extraction. By filtrating the extracted solution, insoluble salts were removed to obtain the aqueous methanol solution. The solution was concentrated by evaporation, and 0.7 g of solid was obtained.

$^1$H-NMR ($D_2O$) δ: 5.21 (1H, s), 5.22 (1H, s), 5.74 (1H, s), 5.76 (1H, s), 7.02-7.68 (30H, broad m); and $^{31}$P-NMR ($D_2O$) δ: −10.8 (large), −13.1 (small), +17.49, +18.8 (P=O, <10%).

Example 3

Synthesis of [RuCl ((R)—$SO_3Na$—$H_8$—BINAP)(p-cymene)]Cl:

Under a nitrogen atmosphere, 0.13 g (0.144 mmol) of (R)—$SO_3Na$—$H_8$—BINAP obtained in Example 1, 38.3 mg (0.0625 mmol) of [$RuCl_2$(p-cymene)]$_2$ and 3 mL of degassed methanol were added into a Schlenk tube, followed by heat ref lux for 2 hours. Next, methanol was evaporated under a reduced pressure to be removed completely, and 0.17 mg of reddish brown fine powder was obtained.

$^{31}$P-NMR ($d_7$-DMF) δ: 39.4-43.0.

Example 4

Synthesis of [RuI((R)—$SO_3Na$—$H_8$—BINAP)(p-cymene)]I:

Under a nitrogen atmosphere, 0.13 g (0.144 mmol) of (R)—$SO_3Na$—$H_8$—BINAP obtained in Example 1, 61 mg (0.0623 mmol) of [$RuI_2$(p-cymene)]$_2$ and 3 mL of degassed methanol were added into a Schlenk tube and stirred at room temperature for 24 hours. Next, methanol was evaporated under reduced pressure to be removed completely, and 0.19 g of reddish brown fine powder was obtained.

$^{31}$P-NMR ($d_6$-DMSO) δ: 41.5-43.4.

Example 5

Synthesis of [RuCl((R)—$SO_3Na$-segphos)(p-cymene)]Cl:

Under a nitrogen atmosphere, 0.11 g (0.122 mmol) of (R)—$SO_3Na$-seghos obtained in Example 2, 36.7 mg (0.06 mmol) of [$RuCl_2$(p-cymene)]$_2$ and 2 mL of degassed methanol were added into a Schlenk tube and stirred at room temperature for 24 hours. Next, methanol was evaporated under reduced pressure to be removed completely, and 0.15 mg of reddish brown fine powder was obtained.

Example 6

Asymmetric Hydrogenation of a Tiglic Acid

Into 100 mL of an autoclave, 3.3 g (33 mmol) of a tiglic acid and 2.42 mg (0.002 mmol) of [RuCl((R)—$SO_3Na$—$H_8$—BINAP)(p-cymene)]Cl obtained in Example 3 were charged and sealed, and an atmosphere in the autoclave was replaced by a nitrogen. 4 mL of degassed diisopropyl ether and 3 mL of degassed distilled water were added thereto, and the atmosphere was replaced by hydrogen, and then the mixture was stirred under a hydrogen pressure of 2.5 MPa at 80° C. for 2 hours. After the reaction, a resulting mixture was cooled to room temperature and the reaction solution was taken out. An organic layer was separated, and was dried over anhydrous magnesium sulfate, followed by filtration and concentration to obtain 2.9 g of a crude (R)-2-methylbutanoic acid. Conversion rate 99.4%; selectivity 100%; optical purity 96.4% ee.

Example 7

Asymmetric Hydrogenation of a Tiglic Acid

In the same condition as Example 6 except that the catalyst was changed to 2.75 mg (2.0 µmol) of [RuI((R)—SO$_3$Na—H$_8$—BINAP)(p-cymene)]I and the solvent was changed to methylene chloride, 3.3 g (33 mmol) of a tiglic acid was asymmetrically hydrogenated to obtain 3.2 g of a crude (R)-2-methylbutanoic acid. Conversion rate 98.4%; selectivity 100%; optical purity 97.4% ee.

Example 8

Asymmetric Hydrogenation of a Tiglic Acid

Into an autoclave under nitrogen atmosphere, 4 g (0.04 mol) of a tiglic acid, 1.2 mg (0.8 µmol) of [RuI((R)—SO$_3$Na—H$_8$—BINAP)(p-cymene)]I and 2 mL of degassed distilled water were added, and the atmosphere was replaced by hydrogen, and then the mixture was stirred under a hydrogen pressure of 2.5 MPa at a reaction temperature of 65° C. for 18 hours. After the reaction, a resulting mixture was extracted with diisopropyl ether and post treatment was carried out in the same way as Example 6 to obtain 3.9 g of a crude (R)-2-methylbutanoic acid. Conversion rate 98.4%; selectivity 100%; optical purity 96.6% ee.

Example 9

Asymmetric Hydrogenation of a Tiglic Acid

Using [RuCl((R)—SO$_3$Na-segphos)(p-cymene)]Cl obtained in Example 5 and in the same condition as Example 6, 3.3 g (33 mmol) of a tiglic acid was asymmetrically hydrogenated to obtain 2.8 9 of a crude (R)-2-methylbutanoic acid. Conversion rate 89.7%; selectivity 100%; optical purity 90.6% ee.

Example 10

Asymmetric Hydrogenation of a Tiglic Acid (Recycling of an Aqueous Phase of a Catalytic Solution)

Into 200 mL of an autoclave under a nitrogen atmosphere, 20 g (199.8 mmol) of a tiglic acid and 13.9 mg (10.0 µmol) of [RuI((R)—SO$_3$Na—H$_8$—BINAP)(p-cymene)]I which had been dissolved in 80 mL of degassed methylene chloride, were added by using a syringe, and methylene chloride was evaporated under a reduced pressure. Next, 40 mL of degassed distilled water was added thereto, and the atmosphere was replaced by hydrogen, and then the mixture was stirred under a hydrogen pressure of 2 MPa at a reaction temperature of 65° C. for 4 hours. After the reaction, 60 mL of degassed heptane was added thereto and stirred. The reaction solution was taken out by aspirating through a syringe with a cock, and was left to stand for 30 minutes with the cock closed. The solution in a syringe was separated to an upper layer of a heptane solution of (R)-2-methylbutanoic acid and a lower layer of an aqueous phase containing a catalyst. The aqueous phase was added into the autoclave again, and was reused for a next reaction. The heptane solution was dried over anhydrous magnesium sulfate, and was concentrated to obtain 39 g of a crude (R)-2-methylbutanoic acid. Conversion rate 99.5%; selectivity 100%; optical purity 97.5% ee.

(The First to the Third Times of Recycling of an Aqueous Phase)

Into an aqueous phase used for the reaction, 20 g (199.8 mmol) of a tiglic acid and 80 mL of degassed methylene chloride were added, and a reaction was carried out for four hours in the same way as the reaction before recycling (the reaction of the first time). After the reaction, a post-treatment was carried out in the same way as the reaction of the first time to obtain 39 g of a crude (R)-2-methylbutanoic acid. Conversion rate 99.3%; selectivity 100%; optical purity 97.3% ee. The same operations were carried out till the third times of recycling.

(The Fourth to the Tenth Times of Recycling of an Aqueous Phase)

Results of the reaction of the first time to the tenth times of recycling are shown in Table 1 below. On and after the fourth time of recycling of an aqueous phase, respectively, 3% of an amount of [RuI((R)—SO$_3$Na—H$_8$—BINAP)(p-cymene)]I in the reaction of the first time were added. Results of the reaction of the first time to the tenth times of recycling are shown in Table 1 below. Each reaction was carried out in a condition that an amount of a tiglic acid as raw material was 20 g, a reaction temperature was 65° C., and a hydrogen pressure was 2 MPa. Further, (S/C) in the Table represents a molar ratio of a tiglic acid/[RuI((R)—SO$_3$Na—H$_8$—BINAP)(p-cymene)]I.

TABLE 1

| Times of recycling | Catalyst (S/C) | Reaction time (hr) | GC purity (%) | Yield (%) | Optical purity (% ee) |
|---|---|---|---|---|---|
| 0 | 20,000 | 4 | 99.3 | 96.0 | 97.5 |
| 1 | — | 4 | 99.6 | 97.5 | 97.6 |
| 2 | — | 5 | 99.4 | 98.1 | 97.5 |
| 3 | — | 5 | 99.5 | 98.5 | 97.4 |
| 4 | +3% | 6 | 99.3 | 98.4 | 97.3 |
| 5 | +3% | 6 | 99.4 | 98.6 | 97.3 |
| 6 | +3% | 8 | 99.4 | 98.5 | 97.4 |
| 7 | +3% | 9 | 99.6 | 98.7 | 97.2 |
| 8 | +3% | 10 | 99.5 | 98.3 | 97.2 |
| 9 | +3% | 12 | 99.3 | 98.6 | 97.3 |
| 10 | +3% | 15 | 99.4 | 98.4 | 97.1 |

Example 11

Asymmetric Hydrogenation of an (E)-2-methyl-2-pentenoic acid.

Into an autoclave under a nitrogen atmosphere, 0.37 g (3.3 mmol) of an (E)-2-methylpentenoic acid, 2.42 mg (1.7 µmol) of [RuI((R)—SO$_3$Na—H$_8$—BINAP)(p-cymene)]I, 0.8 mL of degassed methylene chloride and 3 mL of degassed distilled water were added, and the atmosphere was replaced by hydrogen, and then the mixture was stirred at a reaction temperature of 80° C. under a hydrogen pressure of 2.5 MPa for 3 hours. After the reaction, a resulting mixture was extracted with additional methylene chloride and was treated in the same way as Example 6 to obtain 0.36 9 of a crude (R)-2-methylpentanoic acid. Conversion rate 99.6%; selectivity 99.2%; optical purity 95.0% ee.

Example 12

Asymmetric Hydrogenation of an (E)-2-methyl-2-pentenoic acid

Into an autoclave under a nitrogen atmosphere, 0.377 g (3.3 mmol) of an (E)-2-methyl-2-pentenoic acid, 2.42 mg (2.0 µmol) of [RuI((R)—SO$_3$Na—H$_8$—BINAP)(p-cymene)]I, 0.8 mL of degassed and distilled diisopropyl ether and 3 mL of degassed distilled water were added, and the atmosphere was replaced by hydrogen, and then the mixture was stirred at a reaction temperature of 80° C. under a hydrogen pressure of 2.5 MPa for 3 hours. After the reaction, treatment was carried out in the same way as Example 8 to obtain 0.35 g of a crude (R)-2-methylpentanoic acid. Conversion rate 100%; selectivity 99.6%; optical purity 94.4% ee.

Example 13

Asymmetric Hydrogenation of an (E) -2-methyl-2-hexenoic acid

Into an autoclave under a nitrogen atmosphere, 0.423 g (3.3 mmol) of an (E)-2-methyl-2-hexenoic acid, 2.42 mg (1.7 μmol) of [RuI((R)—SO$_3$Na—H$_8$—BINAP)(p-cymene)]I, 0.8 mL of degassed and distilled methylene chloride and 3 mL of degassed distilled water were added, and the atmosphere was replaced by hydrogen, and then the mixture was stirred at a reaction temperature of 80° C. under a hydrogen pressure of 2.5 MPa for 3 hours. After the reaction, treatment was carried out in the same way as Example 9 to obtain 0.41 g of a crude (R)-2-methylhexanoic acid. Conversion rate 99.6%; selectivity 99.2%;optical purity 93.1% ee.

INDUSTRAL APPLICABILITY

Asymmetric synthesis enabling stereo-selective production of organic compounds in various fields such as perfumes, pharmaceuticals, agricultural chemicals, and liquid crystals, has become industrially extremely important. The present invention provides a transition metal complex for asymmetric synthesis, a catalyst for asymmetric synthesis using it, a phosphine compound therefor, and the like, which are industrially extremely useful.

As a catalyst comprising a transition metal complex according to the present invention is water-soluble, not only separation and recovery after a reaction is easy, and recycling of the catalyst is possible, but also as asymmetric synthesis reaction may be carried out in a water-based solvent, usage amount and wastage amount of a solvent which damages environment, may be reduced, and thus the present invention provides an industrially extremely favorable catalyst.

Accordingly, the present invention has an industrial applicability.

The invention claimed is:

1. A phosphine compound represented by the general formula (1),

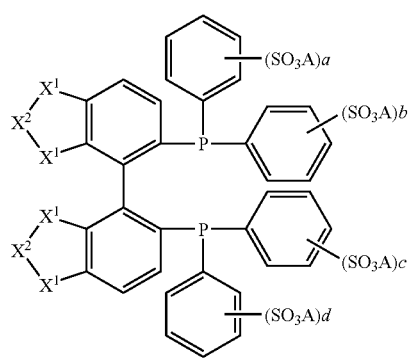

(wherein X$^1$ represents oxygen atom or methylene group, X$^2$ represents methylene group, ethylene group, trimethylene group, 1,2-dimethylethylene group, isopropylidene group, or difluoromethylene group; A represents alkali metal of Group IA of the periodic table, hydrogen atom, or ammonium ion; and a, b, c and d are each an integer of 0 or 1, with the proviso that the sum of a, b, c and d is not 0).

2. The phosphine compound according to claim 1, which is an optically active substance.

3. A transition metal complex, which comprises the phosphine compound according to claim 2 as a ligand.

4. A method for production of an optically active carboxylic acid, wherein asymmetric hydrogenation of a carboxylic acid compound having a carbon-carbon double bond is carried out in the presence of the transition metal complex according to claim 3.

5. The method for production according to claim 4, wherein the transition metal complex is prepared in a reaction system of asymmetric hydrogenation reaction.

6. The method for production according to claim 4 or 5, wherein the transition metal complex is recovered as an aqueous solution from a reaction solution obtained after completion of a reaction, and the aqueous solution is recycled to the reaction system.

7. The method for production according to claim 4 or 5, wherein the carboxylic acid compound having a carbon-carbon double bond, is a compound represented by the general formula (2),

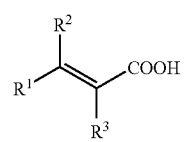

(wherein R$^1$, R$^2$ and R$^3$ represents hydrogen atom, linear, branched or cyclic alkyl group, an aromatic hydrocarbon which may have substituent(s), a heterocyclic group which may have substituent(s), acyloxy group, acylamino group, alkoxy group, aryloxy group, alkoxycarbonyl group, carboxyl group, furyloxy, thienyloxy, or R$^1$ and R$^2$, or R$^1$ and R$^3$ may form a divalent group —(CH$_2$)$_m$—X$^3$—(CH$_2$)$_n$— (where X$^3$ represents methylene group, nitrogen atom, oxygen atom or sulfur atom; and m represents 1 or 2, and n represents an integer of 0 to 3); with a proviso that R$^1$ and R$^2$ are not the same group, and R$^1$ and R$^3$ are not a hydrogen atom at the same time], and the optically active carboxylic acid is represented by the general formula (3),

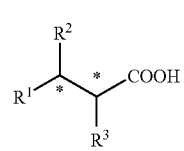

(wherein R$^1$, R$^2$ and R$^3$ represent the same meanings as described above, and * represents one or the both of them being an asymmetric carbon).

8. The method of claim 6, wherein the carboxylic acid compound having a carbon-carbon double bond, is a compound represented by the general formula (2), and the optically active carboxylic acid is represented by the general formula (3),

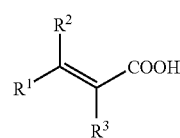

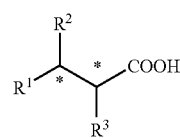

(wherein R$^1$, R$^2$, R$^3$ and * represent the same meaning as described above).

* * * * *